United States Patent
Masuda (10) Patent No.: US 11,678,828 B2
(45) Date of Patent: Jun. 20, 2023

(54) STICK-ON BIOSENSOR (71) Applicant: Nitto Denko Corporation, Ibaraki (JP)

(72) Inventor: Ryota Masuda, Ibaraki (JP)

(73) Assignee: NITTO DENKO CORPORATION, Ibaraki (JP)

(*) Notice: Subject to any disclaimer, the term of this patent is extended or adjusted under 35 U.S.C. 154(b) by 0 days.

(21) Appl. No.: 17/442,030

(22) PCT Filed: Mar. 17, 2020

(86) PCT No.: PCT/JP2020/011725
§ 371 (c)(1),
(2) Date: Sep. 22, 2021

(87) PCT Pub. No.: WO2020/196097
PCT Pub. Date: Oct. 1, 2020

(65) Prior Publication Data
US 2022/0142541 A1    May 12, 2022

(30) Foreign Application Priority Data

Mar. 26, 2019 (JP) .............................. JP2019-058328
Mar. 4, 2020 (JP) .............................. JP2020-036712

(51) Int. Cl.
A61B 5/257 (2021.01)
(52) U.S. Cl.
CPC ................................... A61B 5/257 (2021.01)
(58) Field of Classification Search
CPC ........... A61B 5/24; A61B 5/251; A61B 5/257; A61B 5/6832; A61B 5/683; A61B 5/6801; A61B 5/6833; A61B 5/68335; A61B 5/25
See application file for complete search history.

(56) References Cited

U.S. PATENT DOCUMENTS

2002/0015689 A1    2/2002    Munro et al.
2003/0069510 A1    4/2003    Semler
(Continued)

FOREIGN PATENT DOCUMENTS

CN        104068846 A        10/2014
CN        104665806 A         6/2015
(Continued)

OTHER PUBLICATIONS

Office Action dated Dec. 13, 2021 for corresponding Chinese Patent Application No. 202080021780.1, along with an English machine translation.

(Continued)

Primary Examiner — Adam Z Minchella
(74) Attorney, Agent, or Firm — Hauptman Ham, LLP (57) ABSTRACT A stick-on biosensor capable of acquiring satisfactory biological information is provided. The stick-on biosensor includes a pressure-sensitive adhesive layer and an electrode part, said pressure-sensitive adhesive layer having a stick-on surface to be attached to a subject; a base material layer provided on the side opposite the stick-on surface of the pressure-sensitive adhesive layer; and an electronic device provided on the base material layer and configured to process a biological signal acquired through the electrode part. A structure, which includes the pressure-sensitive adhesive layer, the electrode part, and the base material layer, has a flexural rigidity of 0.010 [MPa·mm$^3$/mm] or higher, and an adhesive strength of the electrode part to adhere to the subject is greater than 0.6 [N/cm$^2$] and less than or equal to 5.0 [N/cm$^2$].

12 Claims, 10 Drawing Sheets

(56) References Cited

U.S. PATENT DOCUMENTS

| | | | |
|---|---|---|---|
| 2003/0224160 A1 | 12/2003 | Murakami et al. | |
| 2004/0054273 A1 | 3/2004 | Finneran et al. | |
| 2009/0076340 A1* | 3/2009 | Libbus | A61B 5/11 |
| | | | 600/509 |
| 2011/0196220 A1 | 8/2011 | Storm | |
| 2012/0157804 A1 | 6/2012 | Rogers et al. | |
| 2012/0165759 A1 | 6/2012 | Rogers et al. | |
| 2013/0140649 A1 | 6/2013 | Rogers et al. | |
| 2014/0148715 A1 | 5/2014 | Alexander et al. | |
| 2014/0296682 A1 | 10/2014 | Wada et al. | |
| 2015/0148646 A1 | 5/2015 | Park et al. | |
| 2019/0328264 A1* | 10/2019 | Jeong | A61B 5/6832 |
| 2019/0365263 A1* | 12/2019 | Raj | A61B 5/6833 |
| 2020/0069203 A1* | 3/2020 | Chang | A61B 5/282 |
| 2020/0093439 A1 | 3/2020 | Yoshioka | |
| 2021/0077304 A1* | 3/2021 | Xu | A61B 5/447 |

FOREIGN PATENT DOCUMENTS

| | | |
|---|---|---|
| EP | 3 616 606 A1 | 3/2020 |
| JP | 2002-536091 A | 10/2002 |
| JP | 2003-342541 A | 12/2003 |
| JP | 2004-83425 A | 3/2004 |
| JP | 2012-10978 A | 1/2012 |
| JP | 2013-514146 A | 4/2013 |
| JP | 2015-512136 A | 4/2015 |
| JP | 2016-166436 A | 9/2016 |
| KR | 10-2015-0065780 A | 6/2015 |
| TW | 201838586 A | 11/2018 |
| WO | 2011/084450 A1 | 7/2011 |
| WO | 2018/198456 A1 | 11/2018 |

OTHER PUBLICATIONS

International Search Report issued for corresponding International Patent Application No. PCT/JP2020/011725 dated Jun. 16, 2020, along with an English translation.

Written Opinion issued for corresponding International Patent Application No. PCT/JP2020/011725 dated Jun. 16, 2020.

The explanation of circumstances concerning accelerated examination filed in corresponding Japanese Patent Application No. 2020-036712 dated May 20, 2020, along with an English translation.

Notice of Reasons for Refusal dated Jul. 7, 2020 issued with respect to the corresponding Japanese Patent Application No. 2020-036712 with machine translation.

Decision to Refusal dated Dec. 15, 2020 issued with respect to the corresponding Japanese Patent Application No. 2020-036712 with English translation.

Decision to Grant issued for corresponding Japanese Patent Application No. 2020-036712 dated Apr. 20, 2021 along with an English translation.

The Extended European Search Report dated Mar. 18, 2022 for corresponding European Application No. 20777488.6.

Yoon et al., "A Flexible and Wearable Human Stress Monitoring Patch", Scientific Reports, vol. 6, No. 1, Mar. 23, 2016, pp. 1-11.

Examination Report No. 1 dated Apr. 19, 2022 for corresponding Australian Patent Application No. 2020249923 (4 pages).

Office Action dated Jun. 16, 2022, for corresponding Indian Patent Application No. 202117042552.

Office Action dated Nov. 17, 2022 for corresponding Canadian Patent Application No. 3,134,253 (4 pages).

* cited by examiner

| sample number | | 1 | 2 | 3 | 4 | 5 | 6 | 7 | 8 | 9 | 10 | 11 | 12 |
|---|---|---|---|---|---|---|---|---|---|---|---|---|---|
| base material | | silicone | silicone | silicone | PET | acrylic | acrylic | acrylic | urethane | urethane | urethane | urethane | urethane |
| thickness of upper part electrode [mm] | | 0.7 | 0.7 | 0.7 | 0.5 | 1.4 | 1.4 | 1.4 | 0.16 | 0.28 | 0.44 | 0.16 | 0.28 |
| elastic modulus [MPa] | | 17 | 17 | 17 | 100 | 3.9 | 8.3 | 1.3 | 100 | 100 | 100 | 100 | 100 |
| total mass [g] | | 7.9 | 7.9 | 7.9 | 5.4 | 13.7 | 13.7 | 13.7 | 5 | 5.1 | 5.2 | 5 | 5.1 |
| area moment of inertia [mm³] | | 0.02858 | 0.02858 | 0.02858 | 0.01042 | 0.22867 | 0.22867 | 0.22867 | 0.00034 | 0.00183 | 0.00710 | 0.00034 | 0.00183 |
| flexural rigidity [MPa·mm³/mm] | | 0.486 | 0.486 | 0.486 | 1.042 | 0.892 | 1.898 | 0.297 | 0.034 | 0.183 | 0.710 | 0.03413 | 0.18293 |
| adhesive strength of probe [N/cm²] | | 1.3 | 3.3 | 2.7 | 1.3 | 1.3 | 1.3 | 1.3 | 1.3 | 1.3 | 1.3 | 3.30000 | 3.30000 |
| during running | baseline fluctuation | ○ | ○ | ○ | ○ | ○ | ○ | ○ | △ | △ | △ | △ | △ |
| | noise | ○ | ○ | ○ | ○ | △ | △ | △ | △ | △ | △ | △ | △ |
| friction from fabric | baseline fluctuation | ○ | ○ | ○ | △ | △ | △ | ○ | △ | △ | △ | △ | △ |
| | noise | ○ | ○ | ○ | △ | △ | △ | △ | △ | △ | △ | △ | △ |
| signal evaluation | | ○ | ○ | ○ | ○ | ○ | ○ | ○ | ○ | ○ | ○ | △ | △ |
| wearing comfort | | ○ | ○ | ○ | ○ | ○ | ○ | ○ | ○ | ○ | ○ | ○ | ○ |
| pain in peeling off | | ○ | ○ | ○ | ○ | ○ | ○ | ○ | ○ | ○ | ○ | ○ | ○ |

FIG.4B

| sample number | 2-1 | 2-2 | 2-3 | 2-4 | 2-5 | 2-6 | 2-7 | 2-8 | 2-9 | 2-10 | 2-11 | 2-12 |
|---|---|---|---|---|---|---|---|---|---|---|---|---|
| base material | acrylic | acrylic | acrylic | acrylic | acrylic | acrylic | silicone | urethane | urethane | urethane | silicone | acrylic |
| thickness of upper part electrode [mm] | 2.1 | 2.8 | 2.1 | 2.8 | 2.1 | 2.8 | 0.7 | 0.04 | 0.08 | 0.08 | 0.7 | 1.4 |
| elastic modulus [MPa] | 3.9 | 3.9 | 8.3 | 8.3 | 1.3 | 1.3 | 17 | 100 | 100 | 100 | 17 | 1.3 |
| total mass [g] | 23.7 | 33.7 | 23.7 | 33.7 | 23.7 | 33.7 | 7.9 | 4.9 | 4.9 | 4.9 | 7.9 | 13.7 |
| area moment of inertia [mm$^3$] | 0.77175 | 1.82933 | 0.77175 | 1.82933 | 0.77175 | 1.82933 | 0.02858 | 0.00001 | 0.00004 | 0.00004 | 0.02858 | 0.22867 |
| flexural rigidity [MPa·mm$^3$/mm] | 3.010 | 7.134 | 6.406 | 15.183 | 1.003 | 2.378 | 0.486 | 0.001 | 0.004 | 0.00427 | 0.486 | 0.297 |
| adhesive strength of probe [N/cm$^2$] | 1.3 | 1.3 | 1.3 | 1.3 | 1.3 | 1.3 | 0.6 | 1.3 | 1.3 | 3.30000 | 0.6 | 0.6 |
| during running | baseline fluctuation | ○ | ○ | ○ | ○ | ○ | ○ | △ | △ | △ | △ | △ | ○ |
| during running | noise | △ | △ | △ | △ | △ | △ | × | △ | △ | △ | × | × |
| friction from fabric | baseline fluctuation | ○ | ○ | ○ | ○ | ○ | ○ | △ | × | × | × | △ | △ |
| friction from fabric | noise | △ | △ | △ | △ | △ | △ | × | × | × | × | × | × |
| signal evaluation | | × | × | × | × | × | × | × | × | × | × | × | × |
| wearing comfort | | ○ | ○ | ○ | ○ | ○ | ○ | ○ | ○ | ○ | ○ | ○ | ○ |
| pain in peeling off | | ○ | ○ | ○ | ○ | ○ | ○ | ○ | ○ | ○ | ○ | ○ | ○ |

FIG.4C

| sample number | 2-13 | 2-14 | 2-15 | 2-16 | 2-17 | 2-18 | 2-19 | 2-20 | 2-21 | 2-22 | 2-23 |
|---|---|---|---|---|---|---|---|---|---|---|---|
| base material | acrylic | acrylic | acrylic | acrylic | acrylic | acrylic | acrylic | acrylic | silicone | silicone | silicone |
| thickness of upper part electrode [mm] | 2.1 | 2.8 | 1.4 | 2.1 | 2.8 | 1.4 | 2.1 | 2.8 | 0.7 | 1.4 | 2.8 |
| elastic modulus [MPa] | 1.3 | 1.3 | 3.9 | 3.9 | 3.9 | 8.3 | 8.3 | 8.3 | 17 | 17 | 17 |
| total mass [g] | 23.7 | 33.7 | 13.7 | 23.7 | 33.7 | 13.7 | 23.7 | 33.7 | 7.9 | 7.9 | 7.9 |
| area moment of inertia [mm$^3$] | 0.77175 | 1.82933 | 0.22867 | 0.77175 | 1.82933 | 0.22867 | 0.77175 | 1.82933 | 0.02858 | 0.22867 | 1.82933 |
| flexural rigidity [MPa·mm$^3$/mm] | 1.003 | 2.378 | 0.892 | 3.010 | 7.134 | 1.898 | 6.406 | 15.183 | 0.48592 | 3.88733 | 31.09867 |
| adhesive strength of probe [N/cm$^2$] | 0.6 | 0.6 | 0.6 | 0.6 | 0.6 | 0.6 | 0.6 | 0.6 | 5.20000 | 5.20000 | 5.20000 |
| during running — baseline fluctuation | ○ | ○ | ○ | ○ | ○ | ○ | ○ | ○ | ○ | ○ | ○ |
| during running — noise | × | × | × | × | × | × | × | × | ○ | ○ | ○ |
| friction from fabric — baseline fluctuation | △ | △ | △ | △ | △ | △ | △ | △ | ○ | ○ | ○ |
| friction from fabric — noise | × | × | × | × | × | × | × | × | ○ | ○ | ○ |
| signal evaluation | × | × | × | × | × | ○ | × | × | ○ | ○ | ○ |
| wearing comfort | × | × | ○ | ○ | × | ○ | ○ | × | ○ | ○ | ○ |
| pain in peeling off | ○ | ○ | ○ | ○ | ○ | ○ | ○ | ○ | × | × | × |

STICK-ON BIOSENSOR

CROSS REFERENCE TO RELATED APPLICATION

This application is a National Stage of International Application No. PCT/JP2020/011725, filed on Mar. 17, 2020, which designates the United States and was published in Japan, and which is based upon and claims priority to Japanese Patent Application No. 2019-058328 filed on Mar. 26, 2019, and No. 2020-036712 filed on Mar. 4, 2020 in the Japan Patent Office. All of the aforementioned applications are hereby incorporated by reference in their entireties.

TECHNICAL FIELD

The present invention relates to a stick-on biosensor.

BACKGROUND ART

Conventionally, a biosensor which uses a biocompatible polymer substrate comprising a plate-like first polymer layer and second polymer layer, an electrode, and a data acquisition module has been known (see, for example, Patent Document 1).

PRIOR ART DOCUMENT(S)

Patent Document 1

Japan Patent Application Laid-open Publication No. 2012-010978

SUMMARY OF THE INVENTION

Technical Problem to be Solved

A biosensor measures various biological information such as electrocardiographic waveforms or brain waves, while being attached onto a living body. If the skin is crinkled during the measurement of biological information by a biosensor, the electrodes may peel off from the living body, or a gap may be produced between the skin and the sensor. In such a case, noise is contained in the biological information, and it may be difficult to acquire satisfactory biological information.

Therefore, an objective is to provide a stick-on biosensor capable of acquiring satisfactory biological information.

Technical Solution(s)

In one aspect of the invention, a stick-on biosensor is provided, which includes a pressure-sensitive adhesive layer and an electrode part, said pressure-sensitive adhesive layer having a stick-on surface to be attached to a subject; a base material layer provided on the side opposite the stick-on surface of the pressure-sensitive adhesive layer; and an electronic device provided on the base material layer and configured to process a biological signal acquired through the electrode part. A structure including the pressure-sensitive adhesive layer, the electrode part, and the base material layer has a flexural rigidity of 0.010 [MPa·mm$^3$/mm] or higher, and the adhesive strength of the electrode part to adhere to the subject is greater than 0.6 [N/cm$^2$] and less than or equal to 5.0 [N/cm$^2$].

In another aspect of the disclosure, the stick-on biosensor is provided, which includes a pressure-sensitive adhesive layer and an electrode part, said pressure-sensitive adhesive layer having a stick-on surface to be attached to a subject; a base material layer provided on the side opposite the stick-on surface of the pressure-sensitive adhesive layer; and an electronic device provided on the base material layer and configured to process a biological signal acquired through the electrode part. A structure including the pressure-sensitive adhesive layer, the electrode part, and the base material layer has a flexural rigidity of 0.034 [MPa·mm$^3$/mm] or higher, and the adhesive strength of the electrode part to adhere to the subject is 1.3 [N/cm$^2$] or more.

Advantageous Effect of the Invention

A stick-on biosensor capable of acquiring satisfactory biological information can be achieved.

EMBODIMENT(S) FOR IMPLEMENTING THE INVENTION

Preferred embodiments for implementing the invention are described below.

Embodiments

Figure 1:
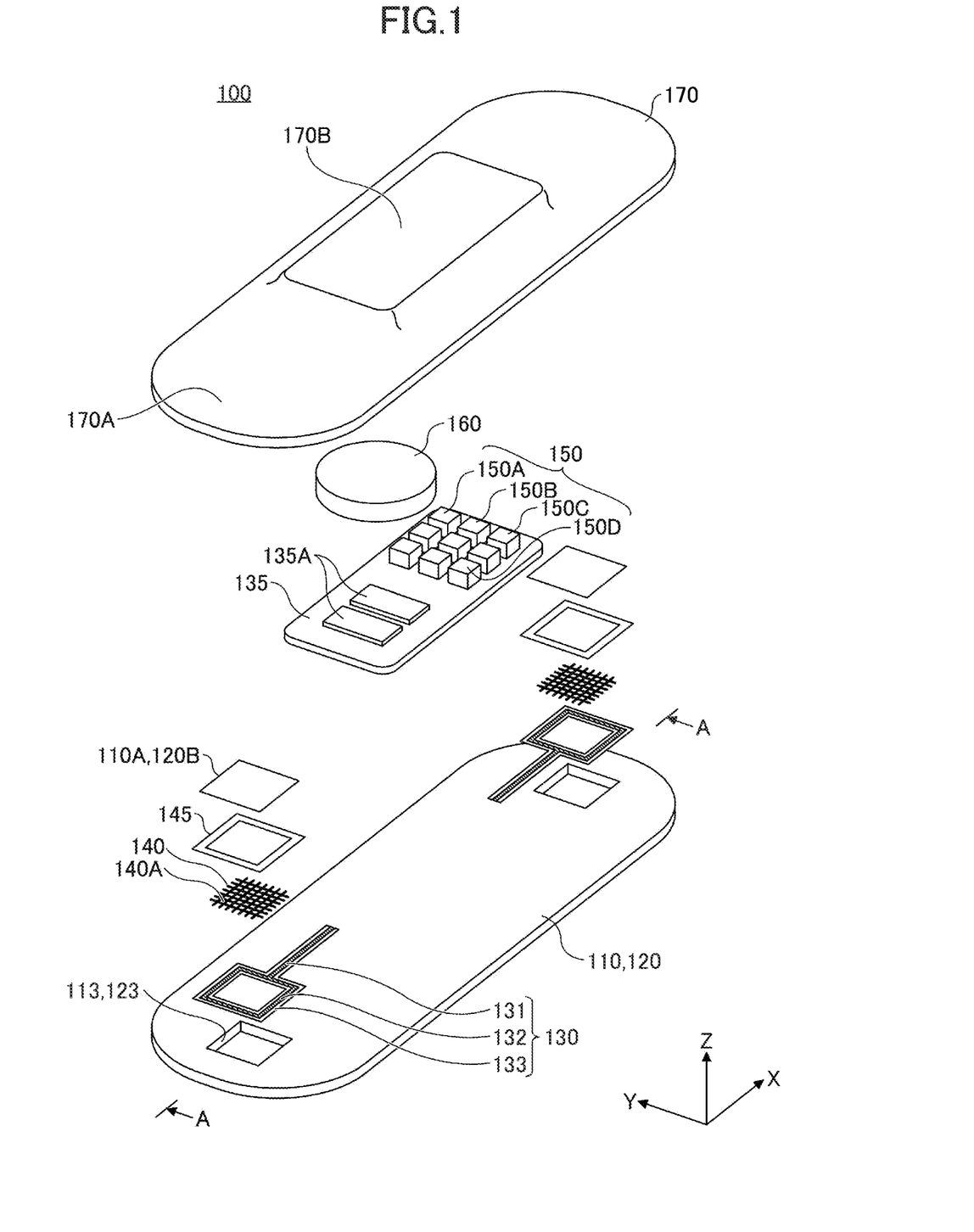
FIG. 1 is an exploded view of a stick-on biosensor 100 according to an embodiment.
Figure 2:
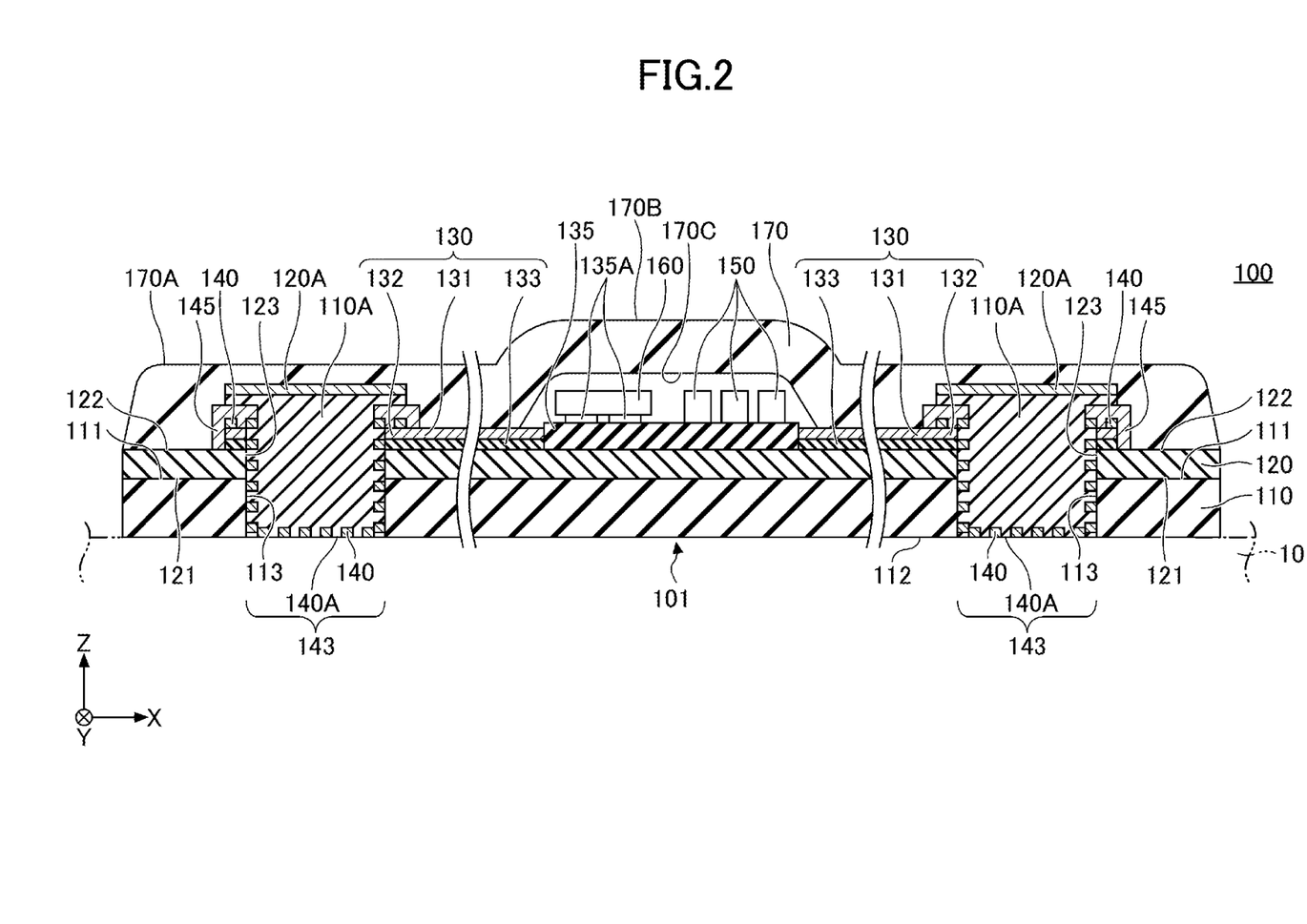
FIG. 2 is a cross-sectional view of the biosensor in the assembled state, taken along the A-A line of FIG. 1.

FIG. 1 is an exploded view of a stick-on biosensor 100 according to an embodiment. FIG. 2 is a cross-sectional view of the stick-on biosensor 100 in the assembled state, taken along the A-A line of FIG. 1. The stick-on biosensor 100 includes a pressure-sensitive adhesive layer 110, a base material layer 120, a circuit unit 130, a substrate 135, a probe 140, a fixing tape 145, an electronic device 150, a battery 160, and a cover 170 as the main components. Of these, the pressure-sensitive adhesive layer 110, the base material layer 120, and a probe part 143 including the probe 140 constitute a structure 101 (shown in FIG. 2).

In the following, the XYZ-coordinate system will be defined to explain the configuration. For convenience of description, the negative direction of the Z axis is referred to as the lower or the bottom side, and the positive direction of the Z axis is referred to as the upper or the top side; however, such directional terms do not mean absolute positional relations.

In the embodiment, the stick-on biosensor 100 is attached onto a living body, i.e., a subject whose biological information is to be measured. A living body may be either a human body or a lifeform other than a human being. The stick-on biosensor 100 can be attached to the skin, the scalp, the forehead, etc. of the living body. The respective components constituting the stick-on biosensor 100 will be described in detail below.

In the following, the electrode brought into contact with a living body (i.e., a subject) is called a probe 140, and a region in which the probe 140 is provided is named a probe part 143. The fixing tape 145 is used as an example of a bonding means. The probe part 143 is an example of an electrode part.

The stick-on biosensor 100 is a sheet-like sensor having a shape of an elongated ellipse in a plan view. The top surface of the stick-on biosensor 100 is covered with a cover 170, which is located on the side opposite the bottom surface (positioned in the −Z direction) of the stick-on biosensor 100 that is attached to the skin 10 of a living body. The bottom surface of the stick-on biosensor 100 is a stick-on surface.

The circuit unit 130 and the substrate 135 are mounted on the upper surface of the base material layer 120. The probe 140 is embedded in the pressure-sensitive adhesive layer 110 so as to be exposed at the lower surface 112 of the pressure-sensitive adhesive layer 110. The lower surface 112 of the pressure-sensitive layer 110 is the bottom surface, and therefore, the stick-on surface of the stick-on biosensor 100 described above.

The pressure-sensitive adhesive layer 110 is a flat adhesive layer, and has a longitudinal axis extending in the X direction, while having a width in the Y direction. The pressure-sensitive adhesive layer 110 is supported by the base material layer 120, and is bonded to the lower surface 121 of the base material layer 120.

The pressure-sensitive adhesive layer 110 has an upper surface 111 and a lower surface 112, as shown in FIG. 2. The upper surface 111 and the lower surface 112 are flat surfaces. The pressure-sensitive adhesive layer 110 is the layer that allows the stick-on biosensor 100 to adhere to a living body. The lower surface 112 sticks to the skin 10 of the living body owing to the adhesiveness. The lower surface 112 serves as the bottom surface of the stick-on biological sensor 100, and is attached to the surface (such as the skin 10) of a living body.

The pressure-sensitive adhesive layer 110 has a through hole 113. The size and the position of the through hole 113 are the same as those of a through hole 123 formed in the base material layer 120 in the plan view, such that the through holes 113 and 123 communicate with each other.

The material of the pressure-sensitive adhesive layer 110 is not particularly limited as long as it has an adhesiveness. For example, a biocompatible adherent material may be used. Examples of the material of the pressure-sensitive adhesive layer 110 include, but are not limited to acrylic pressure-sensitive adhesives and silicone-based pressure-sensitive adhesives. Preferably, an acrylic pressure-sensitive adhesive is used.

Acrylic pressure-sensitive adhesive contains an acrylic polymer as the main component.

Acrylic polymer serves as a pressure-sensitive adhesive component. One example of the acrylic polymer is a polymer produced by polymerizing a monomer component which contains (meth)acrylic acid ester such as isononyl acrylate or methoxyethyl acrylate as a main material, and contains a monomer capable of copolymerization with the (meth)acrylic acid ester as an optional material. The content of the main material in the monomer component is 70 mass % to 99 mass %, and the content of the optional material in the monomer component is 1 mass % to 30 mass %. As the acrylic polymer, (meth)acrylic acid ester-based polymer described in JP-A-2003-342541 may be used.

The acrylic pressure-sensitive adhesive may further contain a carboxylic acid ester.

The carboxylic acid ester contained in the acrylic pressure-sensitive adhesive serves as a modifier for reducing the pressure-sensitive adhesiveness of the acrylic polymer to adjust the adhesive strength of the pressure-sensitive adhesive layer 110. The carboxylic acid ester is miscible or compatible with the acrylic polymer.

An example of the carboxylic acid ester is glyceryl tri-fatty acid ester.

The content of the carboxylic acid ester is preferably 30 to 100 parts by mass, and more preferably 50 to 70 parts by mass, with respect to 100 parts by mass of the acrylic polymer.

The acrylic pressure-sensitive adhesive may contain a cross-linking agent, as necessary. The cross-linking agent is a cross-linker for cross-linking the acrylic polymer. Examples of the cross-linking agent include, but are not limited to polyisocyanate compounds, epoxy compounds, melamine compounds, peroxide compounds, urea compounds, metal alkoxide compounds, metal chelate compounds, metal salt compounds, carbodiimide compounds, oxazoline compounds, aziridine compounds, and amine compounds. These cross-linking agents may be used alone or in combination. The cross-linking agent is preferably a polyisocyanate compound (polyfunctional isocyanate compound).

The content of the cross-linking agent is preferably, for example, 0.001 to 10 parts by mass, and more preferably 0.01 to 1 part by mass with respect to 100 parts by weight of the acrylic polymer.

Preferably, the pressure-sensitive adhesive layer 110 has satisfactory biocompatibility. For example, according to the keratin peeling test performed on the pressure-sensitive adhesive layer 110, the keratin peeled area ratio is preferably 0% to 50%, more preferably 1% to 15%. Within the range of 0% to 50% of the keratin peeled area ratio, the load on the skin 10 (see FIG. 2) can be suppressed when the pressure-sensitive adhesive layer 110 is attached to the skin 10. The keratin peeling test may be performed by the measuring method described in JP-A-2004-83425.

The moisture permeability of the pressure-sensitive adhesive layer 110 is 300 $(g/m^2/day)$ or higher, preferably 600 $(g/m^2/day)$ or higher, and more preferably 1000 $(g/m^2/day)$ or higher. With the moisture permeability of the pressure-sensitive adhesive layer 110 of 300 $(g/m^2/day)$ or higher, the load on the skin 10 (see FIG. 2) can be suppressed when the pressure-sensitive adhesive layer 110 is attached to the skin 10.

The pressure-sensitive adhesive layer 110 can be biocompatible when satisfies at least one of the following conditions; the condition that the keratin peeled area ratio measured by the keratin peeling test is 50% or less, and the condition that the moisture permeability is 300 $(g/m^2/day)$ or higher. It is more preferable for the material of the pressure-sensitive adhesive layer 110 to satisfy both of the conditions. In this case, the pressure-sensitive adhesive layer 110 is more biocompatible in a stable manner.

The thickness of the pressure-sensitive adhesive layer 110 between the upper surface 111 and the lower surface 112 is preferably 10 μm to 300 μm. With the thickness of the pressure-sensitive adhesive layer 110 of 10 μm to 300 μm, the stick-on biosensor 100 can be made thinner, and in particular, the stick-on biosensor 100 except for the electronic device 150 can be made thinner.

The base material layer 120 is a support layer configured to support the pressure-sensitive adhesive layer 110. The pressure-sensitive adhesive layer 110 is bonded to the lower surface 121 of the base material layer 120. The circuit unit 130 and the substrate 135 are provided on the upper surface side of the base material layer 120.

The base material layer 120 is a flat plate-like (or sheet-like) member made of an insulator. The shape of the base material layer 120 in a plan view is the same as the shape of the pressure-sensitive adhesive layer 110, and they are aligned to and stacked with each other.

The base material layer 120 has a lower surface 121 and an upper surface 122, both of which are flat surfaces. The lower surface 121 is in contact with the upper surface 111 of the pressure-sensitive adhesive layer 110 by pressure-sensitive adhesion. The base material layer 120 may be made of a flexible resin having appropriate elasticity, flexibility and toughness. For example, a thermoplastic resin such as polyurethane resin, silicone resin, acrylic resin, polystyrene resin, vinyl chloride resin or polyester resin may be used. The thickness of the base material layer 120 is 1 to 300 μm, preferably 5 to 100 μm, and more preferably 10 to 50 μm.

The circuit unit 130 has a wiring 131, a frame 132, and a substrate 133. The circuit unit 130 is connected to the electrode via the frame 132, and connected to the electronic device 150 via the wiring 131. The stick-on biosensor 100 has two circuit units 130. The wiring 131 and the frame 132 are integrally formed on the upper surface of the substrate 133. The wiring 131 connects the frame 132 to the electronic device 150 and the battery 160.

The wiring 131 and the frame 132 may be made of copper, nickel, gold, or alloys thereof. The thickness of the wiring 131 and the frame 132 is 1 to 100 μm, preferably 1 to 50 μm, and more preferably 5 to 30 μm.

The two circuit units 130 are provided corresponding to two through holes 113 of the pressure-sensitive adhesive layer 110 and two through holes 123 of the base material layer 120. The wiring 131 is connected to the electronic device 150 and the terminal 135A of the battery 160 via the wiring on the substrate 135. The frame 132 is a conductive member shaped in a rectangular loop, which is larger than the through hole 123 of the base material layer 120.

The substrate 133 has the same shape as the wiring 131 and the frame 132 in a plan view. A part of the substrate 133 in which the frame 132 is provided has a rectangular frame area larger than the opening of the through hole 123 of the base material layer 120. The frame 132 and the rectangular frame area of the substrate 133 in which the frame 132 is formed, are placed on the upper surface of the base material layer 120 so as to surround the through hole 123. The substrate 133 is made of an insulator, and a polyimide substrate or film may be used as the substrate 133.

The substrate 135 is an insulative substrate on which the electronic device 150 and the battery 160 are mounted, and it is provided on the upper surface 122 of the base material layer 120. For the substrate 135, a polyimide substrate or film may be used. Wiring and the terminal 135A for the battery 160 are provided on the upper surface of the substrate 135. The wiring of the substrate 135 is connected to the electronic device 150 and the terminal 135A, and is also connected to the wiring 131 of the circuit unit 130.

The probe 140 is an electrode which comes into contact with a subject, specifically, with the skin 10, and configured to detect a biological signal when the pressure-sensitive adhesive layer 110 is attached to the skin 10. The biological signal is an electric signal representing, for example, electrocardiographic waveforms, brain waves (electroencephalogram), pulsing, or the like.

The probe 140 is embedded in the pressure-sensitive adhesive layer 110 so as to be exposed at the lower surface 112 of the pressure-sensitive adhesive layer 110. The probe 140 is not limited to such a form exposed at the lower surface 112 of the pressure-sensitive adhesive layer 110, and it may be fabricated in any suitable forms capable of being in contact with the skin 10. The probe may be integrated with at least a part of the lower surface 112 of the pressure-sensitive adhesive layer 110.

The electrode used as the probe 140 is fabricated using a conductive composition containing at least a conductive polymer and a binder resin, as will be described later. Further, the electrode is fabricated by punching the sheet-like member formed of the conductive composition with a mold or the like, so as to be used as the probe.

The probe 140 has a rectangular shape in a plan view, which is larger than the through holes 113 of the pressure-sensitive adhesive layer 110 and the through holes 123 of the base material layer 120. The probe 140 has holes 140A arranged in a matrix. Along the edges (i.e., the four sides) of the probe 140, ladder-like protrusions extending in the X direction and the Y direction may be formed. The electrode used as the probe 140 may have a predetermined pattern. Examples of the electrode pattern include a mesh pattern, a stripe pattern, or such a pattern that multiple electrodes are exposed at the sticking surface.

The fixing tape 145 is an example of the bonding part of the present embodiment. The fixing tape 145 is, for example, a copper tape shaped into a rectangular loop in a plan view. An adhesive is applied to the lower surface of the fixing tape 145. The fixing tape 145 is provided over the frame 132 along the four sides of the probe 140 so as to surround the openings of the through holes 113 and 123 in a plan view to fix the probe 140 to the frame 132. The fixing tape 145 may be a metal tape other than copper.

The fixing tape 145 may be a non-conductive tape such as a resin tape composed of a non-conductive resin base and an adhesive, in place of a metal tape such as a copper tape. However, a conductive or metal tape may be preferable because the probe 140 can be electrically connected to the frame 132 of the circuit unit 130, while securing the probe 140 onto the frame 132.

The probe 140 is secured to the frame 132 such that the four sides overlap the frame 132, using the fixing tape 145 which is applied so as to cover the periphery of the probe 40. The fixing tape 145 adheres to the frame 132 through the holes 140A of the probe 140.

The pressure-sensitive adhesive layer 110A and the base material layer 120A are placed over the fixing tape 145 and the probe 140, while keeping the four sides of the probe 140 secured to the frame 132 by the fixing tape 145, and pressed downward into the through holes 113 and 123. The probe 140 is pushed into the through holes 113 and 123 along the inner walls thereof, and the pressure-sensitive adhesive layer 110A penetrates through the holes 140A of the probe 140.

The probe 140 is pushed downward until the center area of the probe 140 substantially aligns with the lower surface 112 of the pressure-sensitive adhesive layer 110, while keeping the four edges fixed to the frame 132 by the fixing tape 145. Accordingly, when the probe 140 is pressed against the skin 10 (see FIG. 2) of a living body, the pressure-sensitive adhesive layer 110A adheres to the skin 10 to keep the probe 140 in tight contact with the skin 10.

The thickness of the probe 140 is preferably less than that of the pressure-sensitive adhesive layer 110. The thickness of the probe 140 is preferably 0.1 to 100 µm, more preferably 1 to 50 µm.

The peripheral area of the pressure-sensitive adhesive layer 110A, which forms a rectangular frame area surrounding the center area 11 the plan view, is located on the fixing tape 145. Although in FIG. 2, the upper surface of the pressure-sensitive adhesive layer 110A is substantially flat, the center area may be slightly indented lower than the peripheral area. In either case, the base material layer 120A is superposed on the upper surface of the pressure sensitive adhesive layer 110A.

The pressure-sensitive adhesive layer 110A may be made of the same materials as the pressure-sensitive adhesive layer 110, and the base material layer 120A may be made of the same materials as the base material layer 120. In an alternative, the pressure-sensitive adhesive layer 110A may be made of a different material from the pressure-sensitive adhesive layer 110, or the base material layer 120A may be made of a different material from the base material layer 120.

Although in FIG. 2 the thicknesses of the respective parts are exaggerated for clarifying the structure, the thickness of the pressure-sensitive adhesive layers 110 and 110A is 10 to 300 µm, and the thickness of the base material layers 120 and 120A is 1 to 300 µm in the actual configuration. The thickness of the wiring 131 may be 0.1 to 100 µm, the thickness of the substrate 133 may be about several hundred microns, and the thickness of the fixing tape 145 may be 10 to 300 µm.

With the configuration of FIG. 2, in which the probe 140 and the frame 132 are in direct contact with each other to ensure electrical connection, the fixing tape 145 may be a non-conductive resin tape or the like.

In FIG. 2, the fixing tape 145 covers the edges of the frame 132 and the substrate 133, together with the sides of the probe 140, and it reaches the upper surface of the base material layer 120. However, the fixing tape 145 may not reach the upper surface of the base material layer 120, or may not cover the edges of the substrate 133 and the frame 132, because it is sufficient for the fixing tape 145 to be able to bond the probe 140 and the frame 132.

The substrate 133 and the two substrates 135 may be monolithically formed. In this case, wiring 131, two frames 132, and the terminal 135A are formed on the surface of the monolithic substrate, on which the electronic device 150 and the battery 160 are mounted.

The electrode serving as the probe 140 may be fabricated by thermosetting and molding a conductive composition described below. The conductive composition contains a conductive polymer, a binder resin, and at least one of a cross-linking agent or a plasticizer.

As the conductive polymer, for example, polythiophene, polyacetylene, polypyrrole, polyaniline, polyphenylene vinylene, or the like can be used. Any one, or combinations of two or more of these materials may be used. It is preferable to use, among these, a polythiophene compound. From the viewpoint of lower contact impedance with the living body and higher conductivity, it is preferable to use PEDOT/PSS obtained by doping polystyrene sulfonic acid (poly 4-styrene sulfonate abbreviated as PSS) to poly 3,4-ethylenedioxythiophene (PEDOT).

The content of the conductive polymer is preferably 0.20 to 20 parts by mass with respect to 100 parts by mass of the conductive composition. With the above range of the conductive polymer, satisfactory conductivity, toughness, and flexibility can be imparted to the conductive composition. The content of the conductive polymer is more preferably 2.5 to 1.5 parts by mass, and further preferably 3.0 to 12 parts by mass with respect to the conductive composition.

As the binder resin, either a water-soluble polymer or a water-insoluble polymer can be used. From the viewpoint of compatibility with other components contained in the conductive composition, it is preferable to use a water-soluble polymer for the binder resin. The water-soluble polymer includes a hydrophilic polymer which may not be completely soluble in water, but has hydrophilicity.

For the water-soluble polymer, a hydroxyl group-containing polymer or the like can be used. The hydroxyl group-containing polymer includes saccharides such as agarose, polyvinyl alcohol (PVA), modified polyvinyl alcohol, and a copolymer of acrylic acid and sodium acrylate. Any one or a combination of two or more of these materials may be used. Among these, polyvinyl alcohol and modified polyvinyl alcohol are preferable, and modified polyvinyl alcohol is more preferable.

Examples of the modified polyvinyl alcohol include acetacetyl group-containing polyvinyl alcohol, and diacetone acrylamide modified polyvinyl alcohol. As the diacetone acrylamide-modified polyvinyl alcohol, a diacetone acrylamide-modified polyvinyl alcohol-based resin (DA-modified PVA-based resin) described in JP-A-2016-166436 can be used, for example.

The content of the binder resin is preferably 5 to 140 parts by mass, with respect to 100 parts by mass of the conductive composition. With this content range of the binder resin, conductivity, toughness, and flexibility can be satisfactorily imparted to the conductive composition. The content of the binder resin is more preferably 10 to 100 parts by mass, and further preferably 20 to 70 parts by mass with respect to the conductive composition.

The cross-linking agent and the plasticizer have properties to impart toughness and flexibility to the conductive composition. By imparting flexibility to the molded product of the conductive composition, an elastic electrode can be obtained. Thus, the probe 140 having elasticity is fabricated.

Toughness is a property that achieves both strength and elongation (extensibility). Regarding the toughness, one of the strength and the elongation may be remarkably high, while the other is not remarkably low, such that the strength and the elongation are well balanced.

Flexibility is a property that can suppress damage or breakage even when the molded body (i.e., the electrode sheet) of the conductive composition is bent.

The cross-linking agent crosslinks the binder resin. By mixing the cross-linking agent in the binder resin, the toughness of the conductive composition can be enhanced. Preferably, the cross-linking agent has reactivity with a hydroxyl group. Using such a cross-linking agent, the cross-linking agent can react with the hydroxyl group contained in a binder resin formed of a hydroxyl group-containing polymer.

Examples of the cross-linking agent include zirconium compounds such as zirconium salts; titanium compounds such as titanium salts; borates such as boric acid; isocyanate compounds such as blocked isocyanate; aldehyde compounds such as dialdehyde (e.g., glyoxal); alkoxyl group-containing compounds, and methylol group-containing compounds. Any one or a combination of two or more of these may be used. From the viewpoint of reactivity and safety, a zirconium compound, an isocyanate compound, and an aldehyde compound are preferable.

The content of the cross-linking agent is preferably 0.2 to 80 parts by mass, with respect to 100 parts by mass of the conductive composition. With this content range of the cross-linking agent, satisfactory toughness and flexibility can be imparted to the conductive composition. The content of the cross-linking agent is more preferably 1 to 40 parts by mass, and more preferably 3.0 to 20 parts by mass.

The plasticizer improves the tensile elongation and flexibility of the conductive composition. Examples of the plasticizer include glycerin, ethylene glycol, propylene glycol, sorbitol, polyol compounds with these polymers, and aprotonic compounds such as N-methylpyrrolidone (NMP), dimethylformamide (DMF), NN'-dimethylacetamide (DMAc), or dimethyl sulfoxide (DMSO). Any one or a combination of two or more of these materials may be used. Among these, glycerin is preferable from the viewpoint of compatibility with other components.

The content of the plasticizer is preferably 0.2 to 150 parts by mass, with respect to 100 parts by mass of the conductive composition. With this content range of the plasticizer, satisfactory toughness and flexibility can be imparted to the conductive composition. The content of the plasticizer is more preferably 1.0 to 90 parts by mass, and further preferably 10 to 70 parts by mass with respect to 100 parts by mass of the conductive polymer.

Adding either the cross-linking agent or the plasticizer to the conductive composition is sufficient. By adding the cross-linking agent or the plasticizer in the conductive composition, the toughness and flexibility of the molded product of the conductive composition can be improved.

If the conductive composition contains a cross-linking agent, without containing a plasticizer, the molded product of the conductive composition can have further improved toughness, that is, both tensile strength and tensile elongation, as well as improved flexibility.

If the conductive composition contains a plasticizer, without containing a cross-linking agent, the tensile elongation of the molded product of the conductive composition can be improved, and therefore, toughness is imparted to the molded product of the conductive composition as a whole. The flexibility of the molded product of the conductive composition can also be improved.

It may be preferable that both the cross-linking agent and the plasticizer are contained in the conductive composition. By adding both the cross-linking agent and the plasticizer to the conductive composition, the molded product of the conductive composition has toughness more satisfactorily.

In addition to the above-described components, the conductive composition may contain a surfactant, a softener, a stabilizer, a leveling agent, an antioxidant, an anti-hydrolysis agent, a swelling agent, a thickener, a colorant, a filler, or other known additives, at an appropriate ratio. Examples of the surfactant include silicone-based surfactants.

The conductive composition is prepared by mixing the above-described components in the above-described ratios.

The conductive composition may contain a solvent in an appropriate ratio, as necessary. In this case, an aqueous solution of the conductive composition is appropriately prepared.

The solvent may be an organic solvent or an aqueous solvent. Examples of the organic solvent include ketones such as acetone or methyl ethyl ketone (MEK); esters such as ethyl acetate; ethers such as propylene glycol monomethyl ether; and amides such as N,N-dimethylformamide. Examples of the aqueous solvent include water; and alcohol for methanol, ethanol, propanol, isopropanol, etc. Among these, an aqueous solvent may be preferably used.

At least one of the conductive polymer, the binder resin, and the cross-linking agent may be used in a form of an aqueous solution dissolved in a solvent. In this case, the above-described aqueous solvent can be preferably used.

The electronic device 150 is provided on the upper surface 122 of the base material layer 120 and is electrically connected to the wiring 131. The electronic device 150 processes a biological signal acquired via the electrode used as the probe 140. The electronic device 150 has a rectangular shape in the cross-sectional view. Terminals are provided on the lower surface (−Z direction) of the electronic device 150. Examples of the material for the terminals of the electronic device 150 include solder, conductive paste, or the like.

As shown in FIG. 1, the electronic device 150 may include an application-specific integrated circuit (ASIC) 150A, a micro processing unit (MPU) 150B, a memory 150C, and a wireless communication unit 150D. The electronic device 150 is connected to the probe 140 and the battery 160 via circuit unit 130.

The ASIC 150A includes an analog to digital (A/D) converter. The electronic device 150 is driven by the electric power supplied from the battery 160 and acquires the biological signal measured by the probe 140. The electronic device 150 performs processing such as filtering or digital conversion on the biological signal. The MPU 150B may determine arithmetic means by averaging the biological signals acquired over multiple times, and it stores the biological signals in the memory 150C. The electronic device 150 can continuously acquire biological signals over 24 hours, for example. Because the electronic device 150 may be used for a long period of time to measure biological signals, a configuration for reducing power consumption is employed.

The wireless communication unit 150D is a transceiver used when the biological signals are read out from the memory 150C through radio communication with a test device for evaluation test, at a frequency of, for example, 2.4 GHz. The evaluation test is, for example, a JIS 60601-2-47 standard test. The evaluation test is performed after the assembling of the biological sensor to confirm the performance of the biological sensor which serves as a medical device to detect biological signals. The evaluation test requires that the attenuation ratio of the biological signal output from the biological sensor with respect to the input signal to the biological sensor is less than 5%. This evaluation test is performed on all of the final products.

As shown in FIG. 2, the battery 160 is provided on the upper surface 122 of the base material layer 120. A lead-acid battery, a lithium ion secondary battery, or the like can be used as the battery 160. The battery 160 may be a button cell or a coin battery. The battery 160 has electrical terminals provided on its bottom surface. Two terminals of the battery 160 are connected to the probe 140 and the electronic device 150 via the circuit unit 130. The capacity of the battery 160 is determined so that the electronic device 150 can measure the biological signals for 24 hours or longer, for example.

The cover 170 covers the entirety of the base material layer 120, the circuit unit 130, the substrate 135, the probe 140, the fixing tape 145, the electronic device 150, and the battery 160. The cover 170 has a base 170A and a protrusion 170B protruding from the center of the base 170A in the +Z direction. The base 170A shapes a basic form of the cover 170 in a plan view, and extends in a plane lower than the protrusion 170B. A recess 170C is formed on the bottom side of the protrusion 170B. The bottom surface of the base 170A of the cover 170 is adhered to the upper surface 122 of the base material layer 120. The substrate 135, the electronic device 150, and the battery 160 are housed in the recess 170C. Thus, the cover 170 is provided to the upper surface 122 of the base material layer 120 with the electronic device 150 and the battery 160 accommodated in the recess 170C.

The cover 170 serves not only as a cover protecting the circuit unit 130, the electronic device 150, and the battery 160 provided on the base material layer 120, but also as a shock absorber to protect the internal components from an impact applied from the above to the stick-on biosensor 100. The cover 170 is formed of, for example, silicone rubber, soft resin, urethane, or the like.

Figure 3:
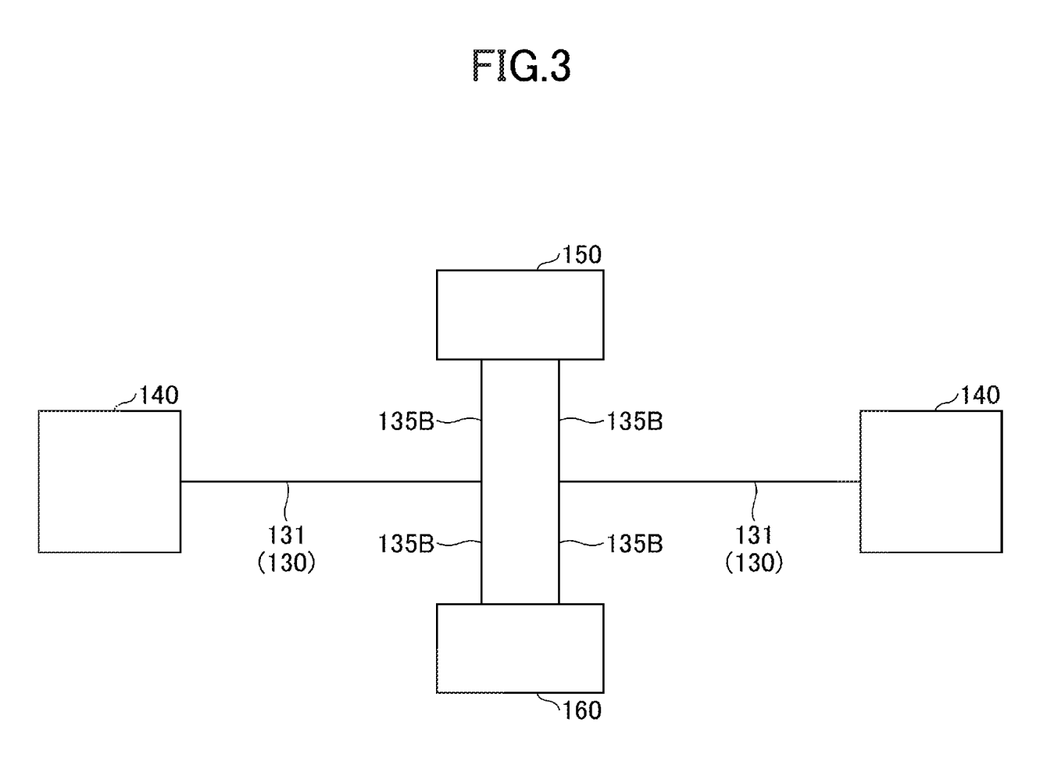
FIG. 3 shows a circuit configuration of the stick-on biosensor 100.

FIG. 3 is a diagram showing a circuit configuration of the stick-on biosensor 100. Each of the probes 140 is connected to the electronic device 150 and the battery 160 via the wiring 131 and the wiring 135B of the substrate 135. The two probes 140 are connected in parallel to the electronic device 150 and the battery 160.

Next, the flexural rigidity of the structure 101, and the adhesive strength of the probe part 143 will be described. The flexural rigidity of the structure 101 is the bending rigidity of the sheet-like structure 101 comprised of the pressure-sensitive adhesive layer 110, the base material layer 120, and the probe 140, which represents the flexural rigidity per unit width. (e.g., 1 mm) expressed in MPa·mm$^3$/mm.

The adhesive strength of the probe part 143 is represented as the adhesive strength per unit area, and expressed in newton per centimeters squared [N/cm$^2$]. The adhesiveness of the probe part 143 may be imparted by the pressure-sensitive adhesive layer 110A. If the probe 140 itself has an adhesiveness, then the adhesive strength of the probe part 143 is determined by the total adhesiveness of the probe 140 and the pressure-sensitive adhesive layer 110A.

Accordingly, the adhesive strength of the probe part 143 is represented as a force acting from the pressure-sensitive adhesive layer 110A to a unit area of the probe part 143 expressed in [N/cm$^2$], or a force acting from both the pressure-sensitive adhesive layer 110A and the probe 140 to a unit area of the probe part 143 expressed in [N/cm$^2$].

The surface of the skin 10 to which the stick-on biosensor 100 is attached may become uneven due to the movements of the living body.

Even if the stick-on biosensor 100 is attached onto a flat skin 10 of the living body in the stationary state, the skin 10 may become wavy or uneven afterward when the living body moves. If the rigidity of the structure 101 and the adhesive strength of the probe part 143 are appropriately high, then the stick-on biosensor 100 strongly sticks to the skin 10, and the skin 10 under the stick-on biosensor 100 will be maintained in the flat state.

This is because the stick-on biosensor 100 which strongly sticks to the skin 10 stretches on the skin 10, while being pressed against the skin 10, thereby preventing the skin 10 from being uneven. In such a case, the probe 140 is in tight contact with the skin 10, and biological signals can be measured in a satisfactory state.

In contrast, if the rigidity of the structure 101 and the adhesive strength of the probe part 143 are insufficient, the skin 10 becomes uneven as the living body moves. The stick-on biosensor 100 is pulled by the unevenness of the skin, and warps on the skin. The stick-on sensor may partially come off from the skin 10. In this case, the probe 140 peels from the skin 10, and biological signals cannot be acquired in satisfactory conditions.

Furthermore, a stick-on biosensor 100 having a certain weight tends to come off from the skin 10 as the living body moves, and there is a risk that biological signals may not be acquired in satisfactory conditions.

Therefore, in the embodiment, a stick-on biosensor 100 is devised such that a satisfactory biological signal can be acquired.

Figure 4A:
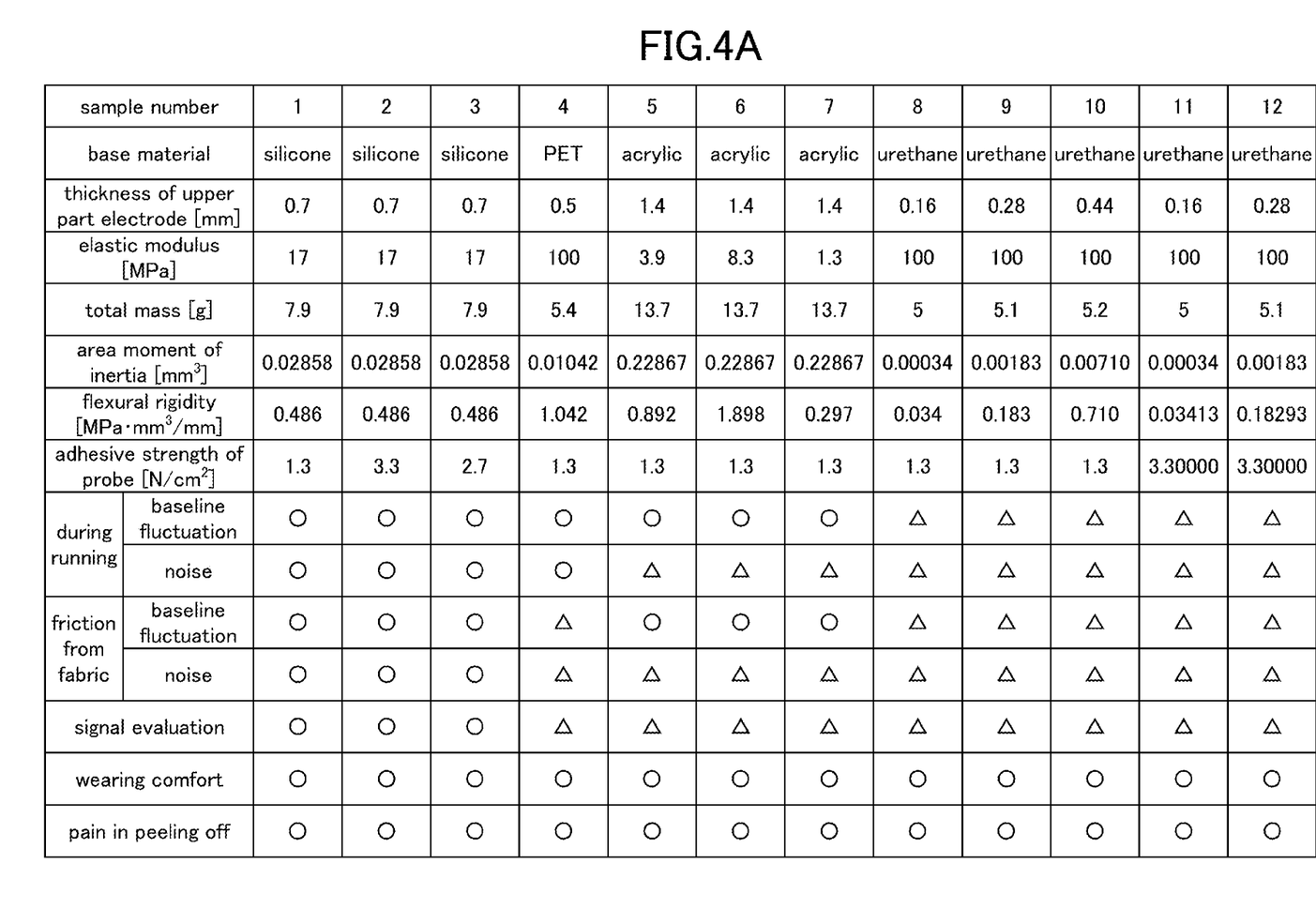
FIG. 4A shows the evaluation result of a plurality of samples.
Figure 4B:
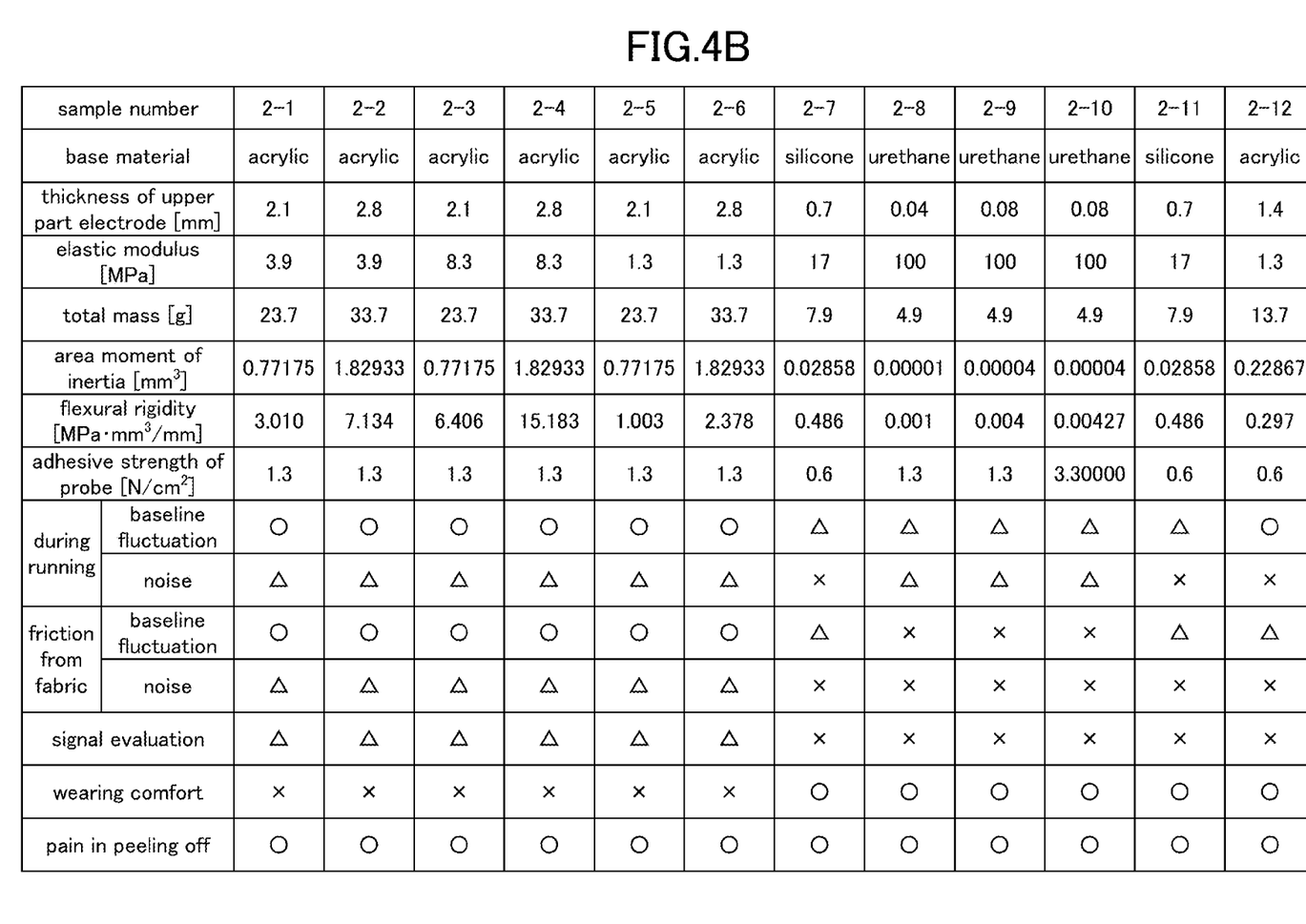
FIG. 4B shows the evaluation result of a plurality of samples.
Figure 4C:
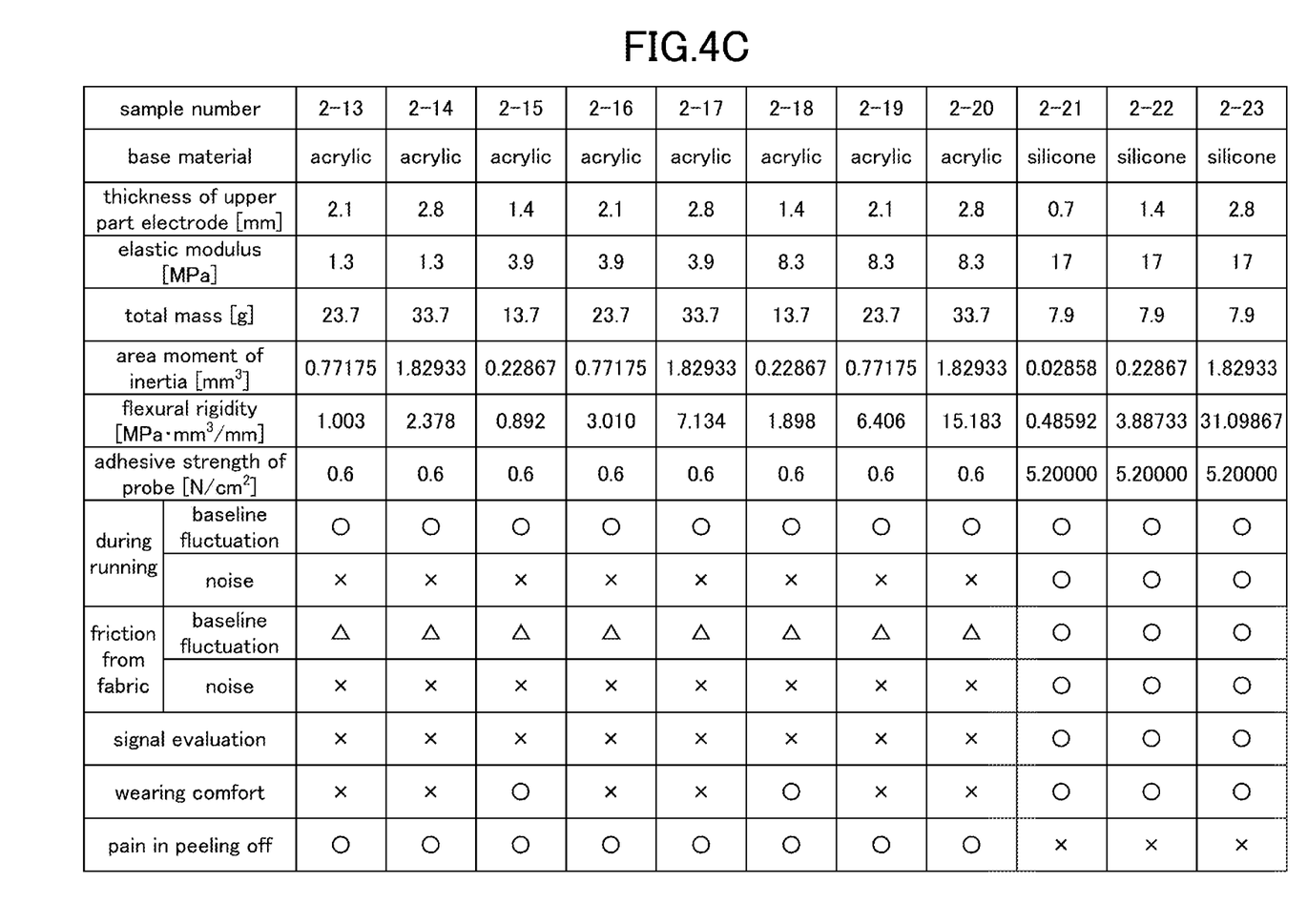
FIG. 4C shows the evaluation result of a plurality of samples.

FIG. 4A to FIG. 4C show evaluation results of the stick-on biosensor 100, which are acquired while changing the values of the material, the thickness [mm] of the upper part of the electrode, the elastic modulus [MPa], the area moment of inertia [mm$^3$], the flexural rigidity [MPa·mm$^3$/mm], and the adhesive strength [N/cm$^2$] of the base material layer 120.

The thickness of the upper part of the electrode represents the total thickness of the pressure-sensitive adhesive layer 110A and the base material layer 120 positioned above the probe 140 in the structure 101 (namely, the thickness determined by subtracting the thickness of the probe 140 from the thickness of the structure 101). The elastic modulus is that of the structure 101. The area moment of inertia is the area moment of inertia per unit width of the structure 101, which indicates the difficulty of deformation with respect to the bending moment. The flexural rigidity is the flexural rigidity per unit width of the structure 101. The adhesive strength is the adhesive strength of the probe part 143 as described above.

Thirty five (35) samples of the stick-on biosensor 100 were prepared and evaluated, while changing the values of the above-described parameters. Seven items, namely, baseline fluctuation and noise of ECG waveforms measured by the stick-on biosensor 100 attached to the chest during running, baseline fluctuation and noise of ECG waveforms due to friction from the clothes of the subject who wears the stick-on biosensor 100 on the chest, signal evaluation, wearing comfort, and pain in peeling off are evaluated. Based on the total evaluation results of the seven items, the thirty five samples are grouped into the first group (samples 1 to 12) suitably used as the stick-on sensor 100, and the second group (samples 2-1 to 2-23) unsuitable for practical use.

Among the evaluation items, "during running" refers to the state in which the subject with the stick-on biosensor 100 attached to the chest is running. "Friction from fabric" refers to the state in which the neckline of the clothes the subject is wearing is shaken up and down such that the clothes are rubbed against the stick-on biosensor 100 attached to the chest of the subject.

Figure 5A:
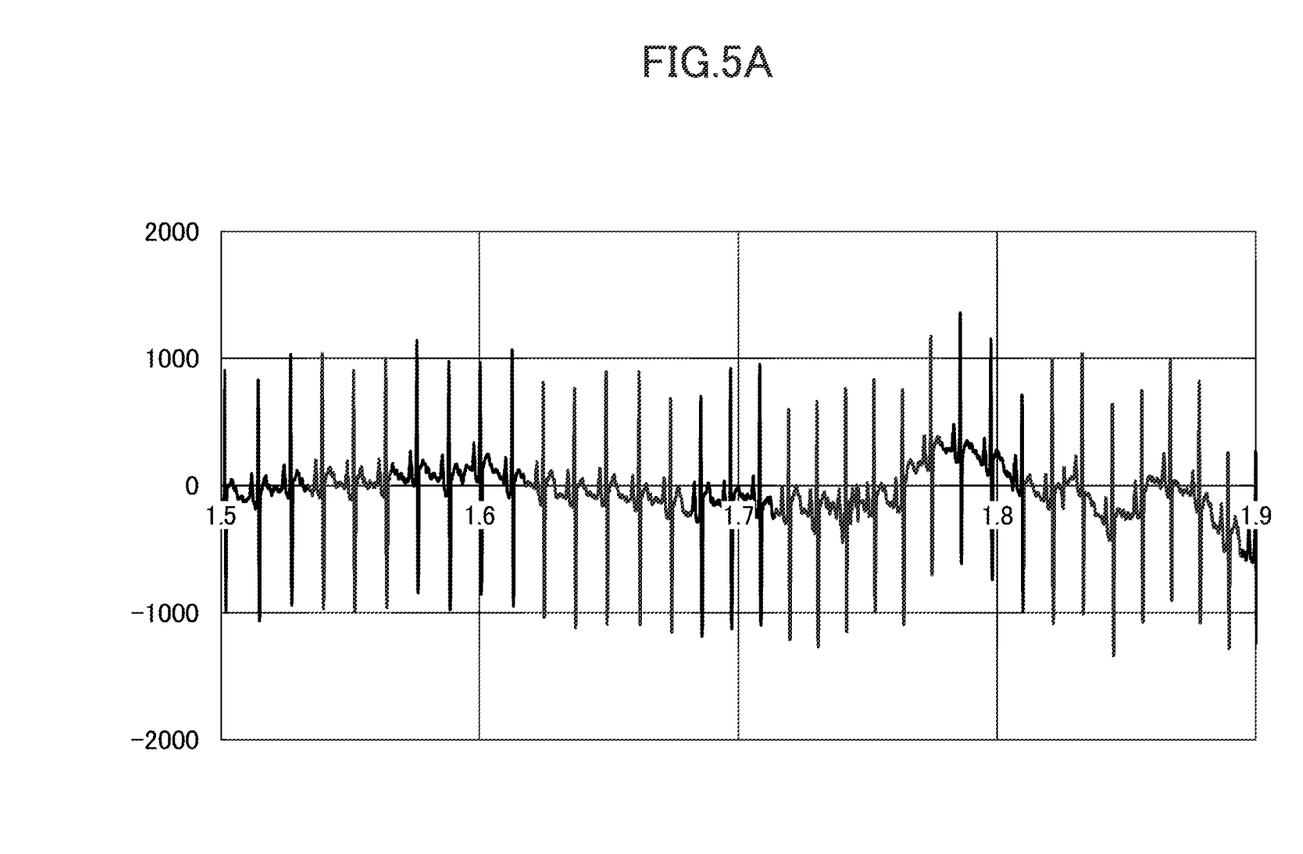
FIG. 5A shows how the baseline fluctuation is evaluated.
Figure 5B:
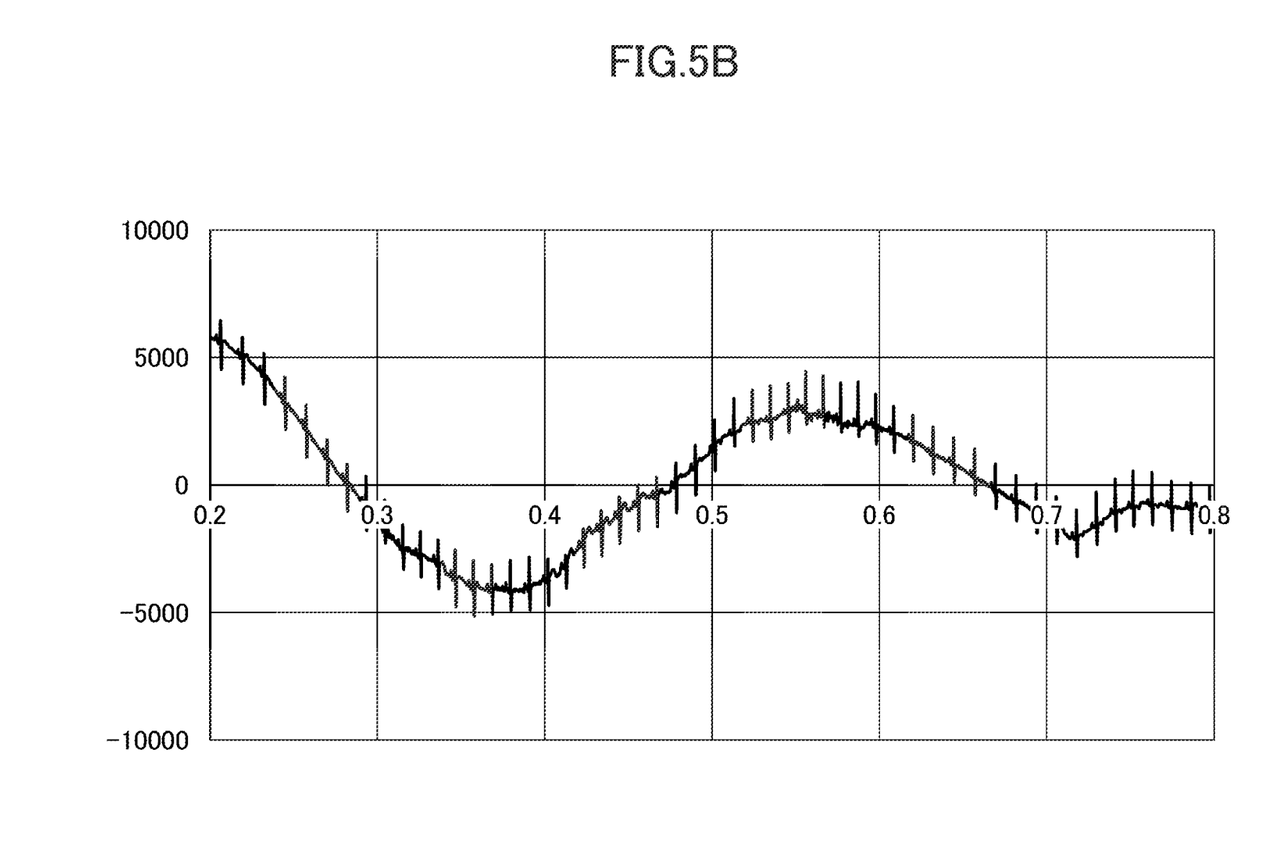
FIG. 5B shows how the baseline fluctuation is evaluated.

The baseline fluctuation is observed from the electrocardiographic waveform obtained from the stick-on biosensor 100, as shown in FIG. 5A and FIG. 5B. As in FIG. 5A, the case where the fluctuation of the baseline is small and the electrocardiographic data can be stably obtained is evaluated as good and marked with an open circle (○). The case where the baseline fluctuates within a certain range as shown in FIG. 5B is evaluated as acceptable and marked with an open triangle (Δ). The case where the baseline fluctuates beyond the range shown in FIG. 5B is evaluated as not good and marked with a cross mark (x).

The signal evaluation includes assessment of degree of baseline fluctuation, whether the electrocardiographic waveform can be confirmed, and whether the electrocardiographic waveform is observed without being buried in noise. Wearing comfort is a subjective evaluation as to how the subject feels when wearing the stick-on biosensor 100. The pain in peeling off indicates whether the subject feels pain when the stick-on biosensor 100 is peeled off from the skin after the measurement.

The pain in peeling off is evaluated by verbal rating scale (VRS). VRS is assessment using terms describing three levels of pain together with scores, and choosing one of "no pain", "slightly painful", and "painful". In this embodiment, "no pain" and "slightly painful" are assessed as satisfactory and marked with an open circle good (○), and "painful" is assessed as poor and marked with a cross mark (x). The "painful" case is assessed as poor because the skin is pulled when the probe electrode is peeled off, which causes pain.

As to the material of the base material layer 120, silicone rubber, polyethylene terephthalate (PET), acrylic resin, and urethane rubber are used. The thickness [mm] of the upper part electrode, the elastic modulus [MPa], the flexural rigidity [MPa·mm³/mm], and the adhesive strength [N/cm²] are set to various values, as shown in FIG. 4A to FIG. 4C.

The evaluation results, except for the pain assessment, are indicated as three different levels, namely, good (marked with a circle), acceptable (marked with triangle), and poor (marked with cross mark). These samples marked with circles or triangles (evaluated as good or acceptable) for all the seven items successfully pass the evaluation test of the stick-on biosensor 100. Samples 1-12 of the first group have passed the test. A sample having a cross mark in any one of the seven items is inappropriate for the stick-on biosensor 100. Samples 2-1 to 2-23 of the second group do not pass the test.

Figure 6:
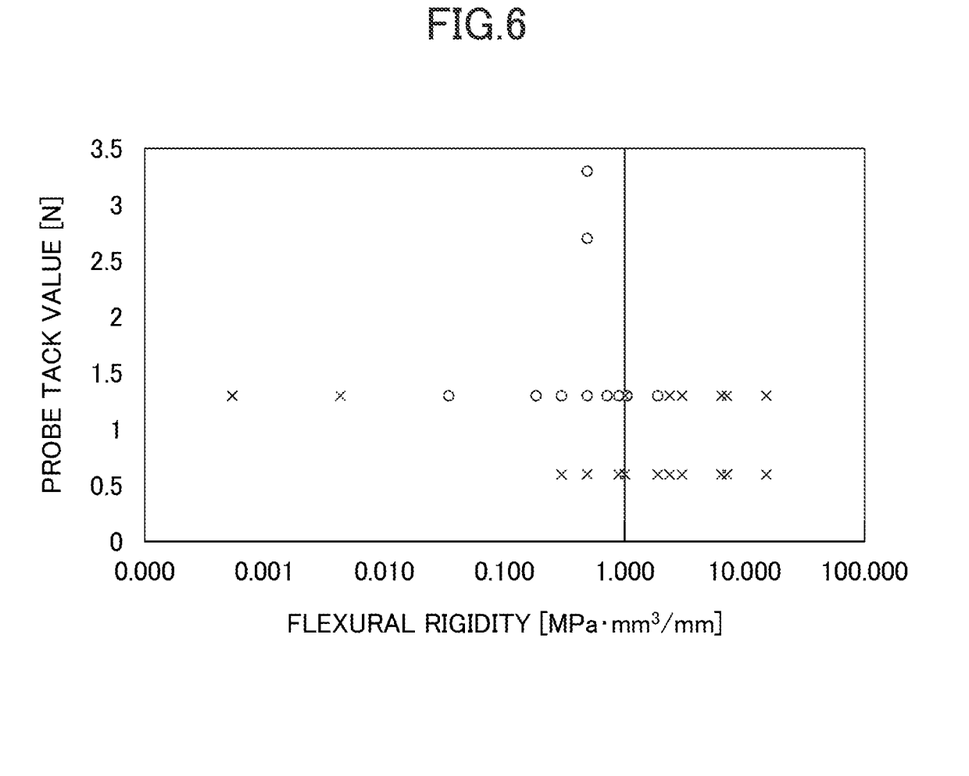
FIG. 6 is a chart summarizing the evaluation results of FIG. 4A to FIG. 4C.

FIG. 6 is a chart summarizing the evaluation results of FIG. 4A to FIG. 4C. The horizontal axis represents the flexural rigidity, and the vertical axis represents the adhesive strength of the probe part 143. In FIG. 6, the acceptable samples 1 to 10 among the 35 samples are indicated by circles, and the unacceptable samples 2-1 to 2-9 and 2-11 to 2-20 are indicated by cross marks.

It is derived from FIG. 6 that the flexural rigidity of the samples 1 to 10 is 0.010 or higher, more preferably 0.034 or higher, and that the adhesive strength of the probe part 143 is greater than 0.6 and less than or equal to 3.5. Samples 2-1 to 2-6, which are evaluated as unacceptable, have a flexural rigidity of 0.034 or higher, and the adhesive strength of the probe part 143 is within the above-described range (greater than 0.6 and less than or equal to 3.5). However, these samples have poor wearing comfort and are marked with cross marks. The reason for the poor wearing comfort is that the flexural rigidity is too strong and a strong tensile stress is applied to the skin 10.

Therefore, the upper limit of the flexural rigidity is 1.898, which is the maximum value among the samples 1 to 9. Because the evaluation of the wearing comfort is subjective, samples 2-1 to 2-6 may be grouped in a feasible group as quasi-acceptable samples.

Focusing on samples 1 to 10, 2-1 to 2-9, and 2-11 to 2-20, in order to allow the stick-on biosensor 100 to acquire satisfactory biological information in spite of movements of the living body, the flexural rigidity of the structure 101 is set to 0.034 or higher, and the adhesive strength of the probe part 143 is set to the range greater than 0.6 and less than or equal to 3.5, preferably set to the range from 1.0 to 2.5, and more preferably set in the vicinity of 1.3. If the flexural rigidity of the structure 101 is within the range greater than 0.034 and less than or equal to 1.898, the wearing comfort will be satisfactory.

Figure 7:
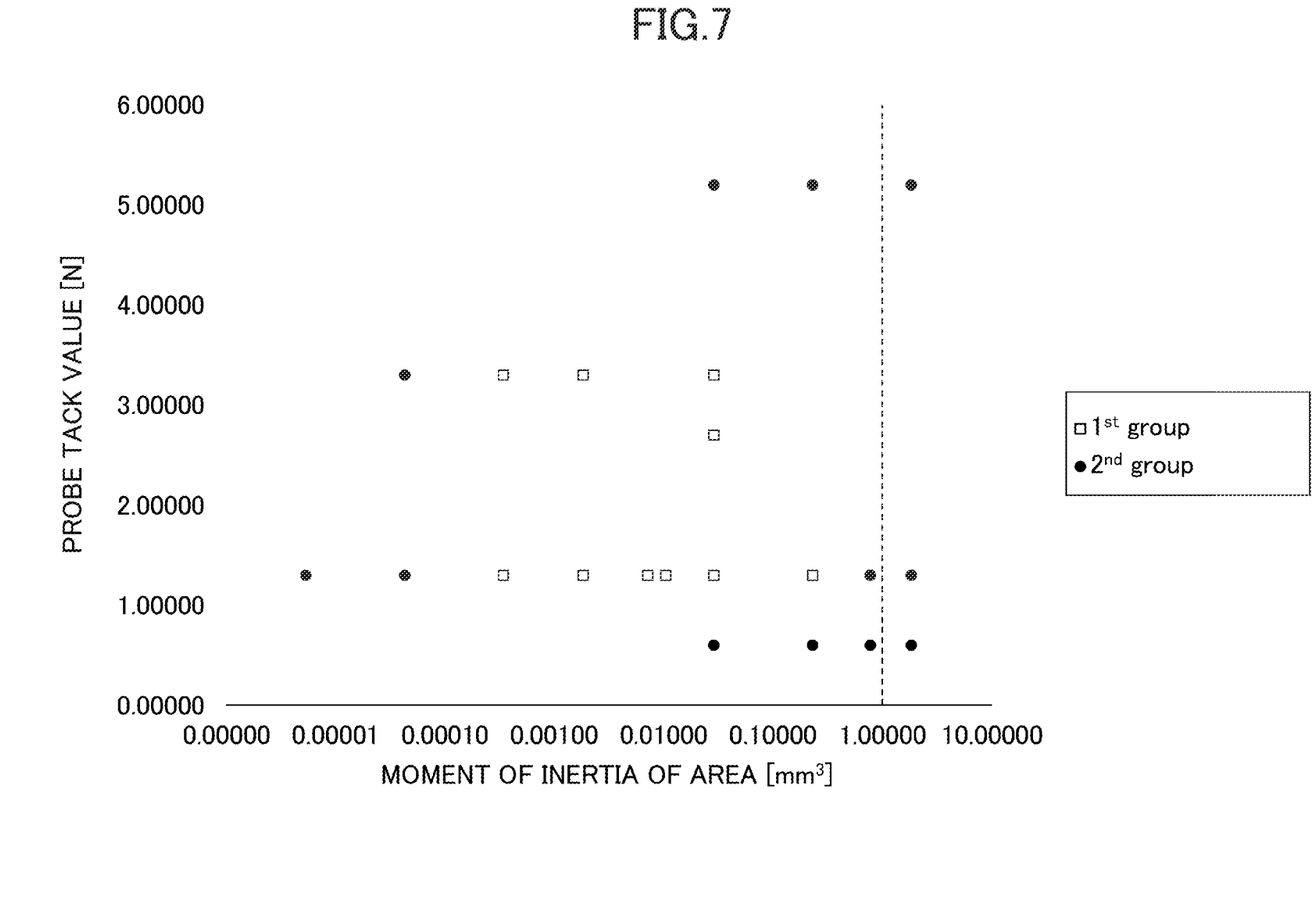
FIG. 7 is a chart summarizing the evaluation results of FIG. 4A to FIG. 4C.

FIG. 7 is another chart summarizing the evaluation results of FIG. 4A to FIG. 4C. The horizontal axis represents the area moment of inertia per unit width, and the vertical axis represents the adhesive strength of the probe part 143. Among the 35 samples, samples 1 to 12 of the first group are indicated by squares, and samples 2-1 to 2-23 of the second group are indicated by black circles. The total number of the symbols appears to be less than 35 because there are several samples having the same or very close measurements.

In FIG. 7, the three samples having an adhesive strength exceeding 5.0 [N/cm²] are samples 2-21 to 2-23. The adhesive strength of these samples is too strong, which causes pain when the stick-on biosensor 100 is peeled off. It is desirable that the adhesive strength is 5.0 [N/cm²] or less.

On the other hand, the samples having an adhesive strength of 0.6 [N/cm²] are samples 2-11 to 2-20. The adhesive strength of these samples is too low, causing a high noise, which makes it difficult to acquire accurate electrocardiographic data. Hence, the adhesive strength is preferably in the range greater than 0.6 [N/cm²] and less than or equal to 5.0 [N/cm²]. More preferably, as described above, the adhesive strength ranges from 1.0 [N/cm²] to 3.5 [N/cm²], and still more preferably ranges from 1.3 [N/cm²] to 3.3 [N/cm²].

From FIG. 7, the area moment of inertia is preferably in the range excluding the second group, that is, in the range from 0.0001 [mm³] to 0.7000 [mm³], and more preferably from 0.0003 [mm³] to 0.2300 [mm³].

From the foregoing, the stick-on biosensor 100 of the embodiment can acquire a satisfactory biological signal (or biological information), even if the living body moves during measurement, by setting the flexural rigidity of the structure 101 and the adhesive force of the probe part 143 to the above-described values.

Thus, a stick-on biosensor 100 capable of acquiring satisfactory biological information can be provided.

Although the stick-on biosensor has been described above based on particular examples, the present invention is not limited to the above-described specific embodiments, and various modification and substitutions are available without departing from the scope of the appended claims.

LISTING OF SYMBOLS

100: stick-on biosensor
110: pressure-sensitive adhesive layer
120: base material layer
130: circuit unit
140: probe
145: fixing tape
150: electronic device
160: battery
170: cover

What is claimed is:
1. A stick-on biosensor comprising:
a pressure-sensitive adhesive layer and an electrode part, said pressure-sensitive adhesive layer having a stick-on surface to be attached to a subject;
a base material layer provided on the side opposite the stick-on surface of the pressure-sensitive adhesive layer; and
an electronic device provided on the base material layer and configured to process a biological signal acquired through the electrode part,
wherein
a structure composed of the pressure-sensitive adhesive layer, the electrode part, and the base material layer has a flexural rigidity per unit width ranging from 0.034 [MPa·mm3/mm] to 1.898 [MPa·mm3/mm],
an area moment of inertia per unit width of the structure ranges from 0.00034 [mm3] to 0.22867 [mm3],
the electrode part is formed of a conductive polymer and exposed at the stick-on surface of the pressure-sensitive adhesive layer, and an adhesive strength of the electrode part imparted by the stick-on surface of the pressure sensitive adhesive layer to adhere to the subject is greater than 1.3 [N/cm2] and less than or equal to 3.3 [N/cm2].

2. The stick-on biosensor as claimed in claim 1, wherein the electrode part is integrated with at least a part of the stick-on surface of the pressure-sensitive adhesive layer.

3. The stick-on biosensor as claimed in claim 1, wherein the electrode part has an electrode with a shape of a predetermined pattern.

4. The stick-on biosensor as claimed in claim 1, further comprising:
a circuit that connects the electrode part and the electronic device.

5. The stick-on biosensor as claimed in claim 4, further comprising:
a substrate on which the circuit is formed, the substrate and the circuit being mounted on a top surface of the base material layer.

6. The stick-on biosensor as claimed in claim 5, wherein the substrate is a first substrate and the circuit is a first circuit, and the stick-on bio sensor further comprises:
a second substrate on which a second circuit is formed, the second substrate and the second circuit being provided on the top surface of the base material layer.

7. A stick-on biosensor comprising:
a pressure-sensitive adhesive layer and an electrode part, said pressure-sensitive adhesive layer having a stick-on surface to be attached to a subject;
a base material layer provided on the side opposite the stick-on surface of the pressure-sensitive adhesive layer; and
an electronic device provided on the base material layer and configured to process a biological signal acquired through the electrode part,
wherein
a structure composed of the pressure-sensitive adhesive layer, the electrode part, and the base material layer has a flexural rigidity per unit width ranging from 0.486 [MPa·mm$^3$/mm] to 1.042 [MPa·mm$^3$/mm],
an area moment of inertia per unit width of the structure ranges from 0.01042 [mm$^3$] to 0.02858 [mm$^3$],
the electrode part is formed of a conductive polymer and exposed at the stick-on surface of the pressure-sensitive adhesive layer, and
an adhesive strength of the electrode part imparted ley the stick-on surface of the pressure sensitive adhesive layer to adhere to the subject ranges from 1.3 [N/cm$^2$] to 3.3 [N/cm$^2$].

8. The stick-on biosensor as claimed in claim 7, wherein the electrode part is integrated with at least a part of the stick-on surface of the pressure-sensitive adhesive layer.

9. The stick-on biosensor as claimed in claim 7, wherein the electrode part has an electrode with a shape of a predetermined pattern.

10. The stick-on biosensor as claimed in claim 7, further comprising:
a circuit that connects the electrode part and the electronic device.

11. The stick-on biosensor as claimed in claim 10, further comprising:
a substrate on which the circuit is formed, the substrate and the circuit being mounted on a top surface of the base material layer.

12. The stick-on biosensor as claimed in claim 11, wherein the substrate is a first substrate and the circuit is a first circuit, and the stick-on bio sensor further comprises:
a second substrate on which a second circuit is formed, the second substrate and the second circuit being provided on the top surface of the base material layer.

* * * * *